United States Patent
Baeke

(10) Patent No.: US 6,203,570 B1
(45) Date of Patent: Mar. 20, 2001

(54) BREAST IMPLANT WITH POSITION LOCK

(76) Inventor: John L. Baeke, 10522 W. 148th St., Overland Park, KS (US) 66221

( * ) Notice: Subject to any disclaimer, the term of this patent is extended or adjusted under 35 U.S.C. 154(b) by 0 days.

(21) Appl. No.: 09/449,454

(22) Filed: Nov. 24, 1999

(51) Int. Cl.⁷ .................................................. A61F 2/12
(52) U.S. Cl. .................................................. 623/8; 623/7
(58) Field of Search ................................. 623/7, 8

(56) References Cited

U.S. PATENT DOCUMENTS

| | | |
|---|---|---|
| 4,507,810 | 4/1985 | Bartholdson . |
| 4,636,213 | 1/1987 | Pakiam . |
| 4,795,463 | 1/1989 | Gerow . |
| 4,863,470 * | 9/1989 | Carter ........................................ 623/8 |
| 4,955,909 | 9/1990 | Ersek . |
| 4,995,882 | 2/1991 | Destouet et al. . |
| 5,071,433 * | 12/1991 | Naestoft et al. .......................... 623/7 |
| 5,246,454 | 9/1993 | Peterson . |
| 5,300,120 | 4/1994 | Knapp et al. . |
| 5,352,307 * | 10/1994 | Wild ........................................ 156/66 |
| 5,500,017 | 3/1996 | Bretz et al. . |
| 5,534,023 * | 7/1996 | Henley ..................................... 623/8 |
| 5,545,217 | 8/1996 | Offray et al. . |
| 5,697,974 * | 12/1997 | Wang ....................................... 623/7 |
| 5,716,407 * | 2/1998 | Knapp et al. ........................ 623/11.11 |
| 5,843,189 | 12/1998 | Perouse . |
| 5,935,164 | 8/1999 | Iversen . |
| 6,074,420 * | 6/2000 | Eaton ...................................... 623/7 |

OTHER PUBLICATIONS

Surgitek catalog; (2 pages).
Bristol–Meyers Dow Corning catalog (1 page).

* cited by examiner

Primary Examiner—David H. Willse
Assistant Examiner—Suzette J. Jackson
(74) Attorney, Agent, or Firm—Chase & Yakimo, L.C.

(57) ABSTRACT

An improved breast implant prosthesis provides fastening components to anchor the implant to retroglandular or retromuscular tissue and secure the implant in place. Location markers are also provided to ensure correct orientation of the prosthesis during the augmentation mammaplasty procedure and provide postoperative orientation information without the use of invasive procedures.

35 Claims, 6 Drawing Sheets

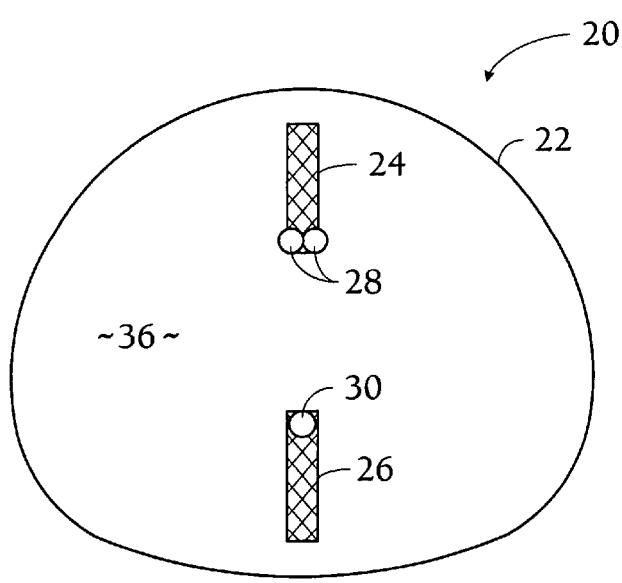
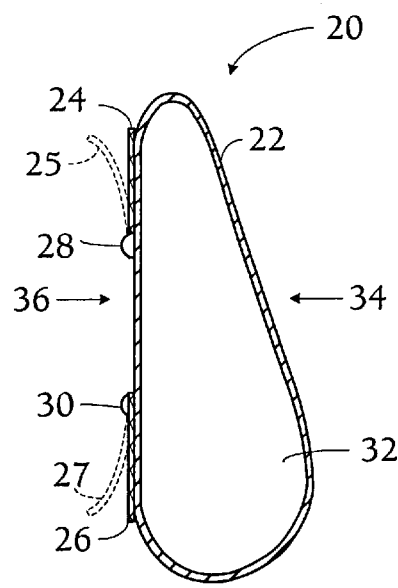
Fig. 1  Fig. 2
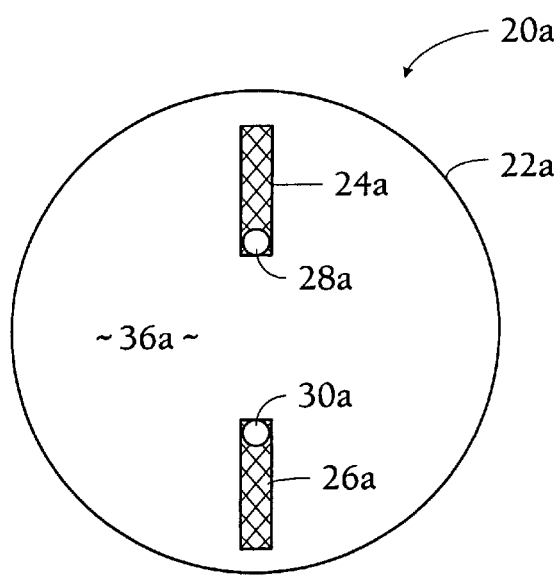
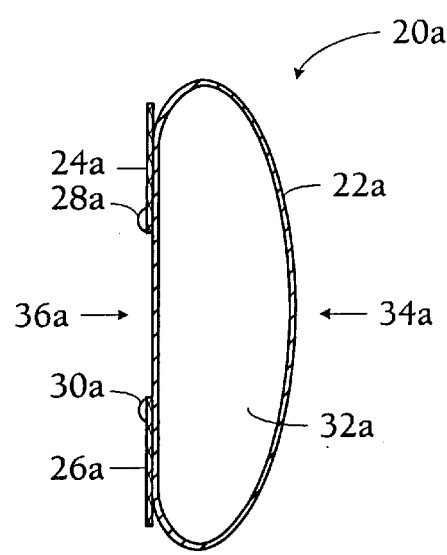
Fig. 3  Fig. 4

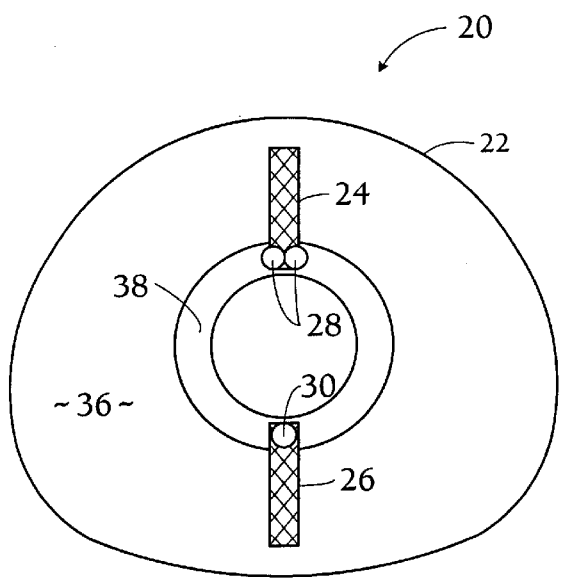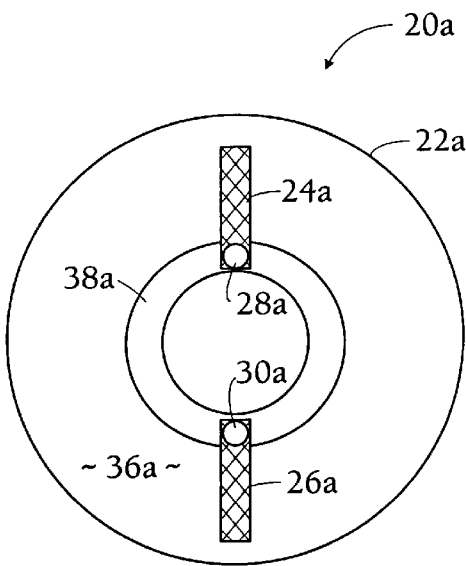
Fig. 5  Fig. 6
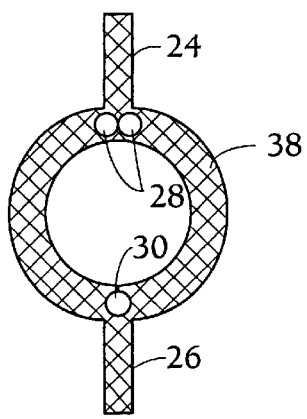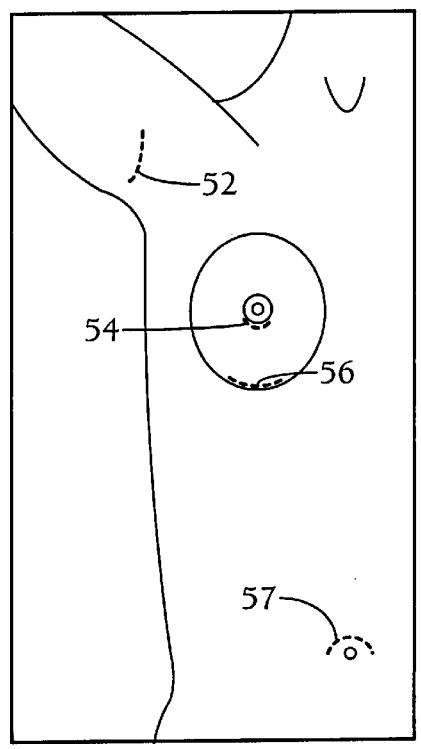
Fig. 7  Fig. 15

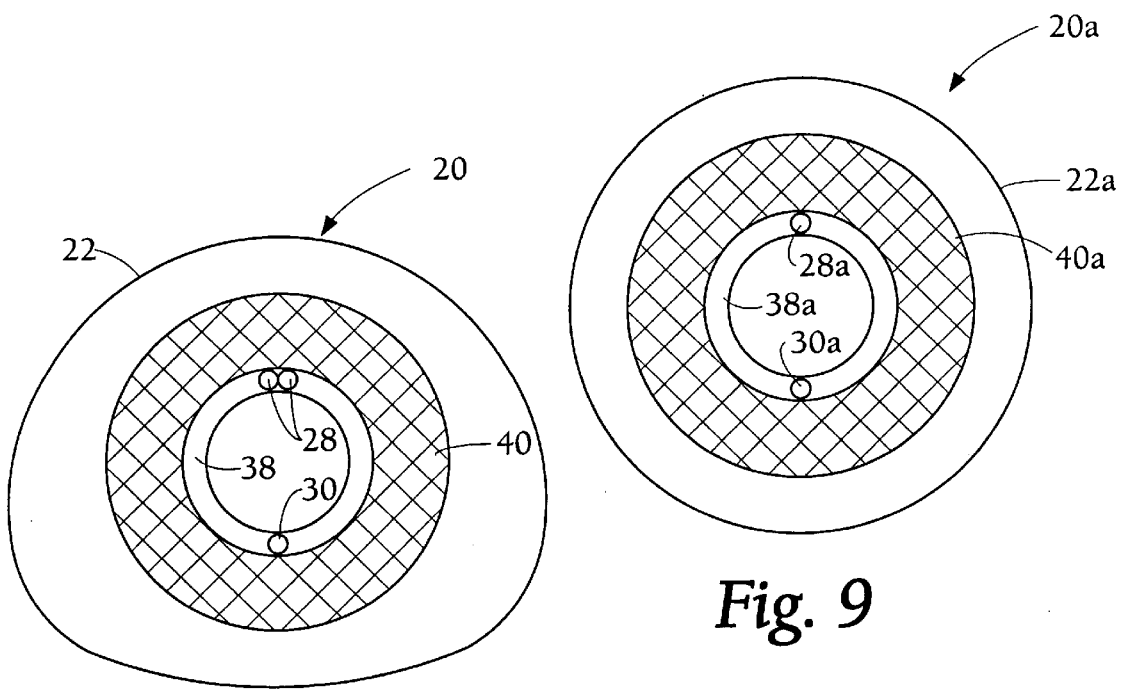
Fig. 8
Fig. 9
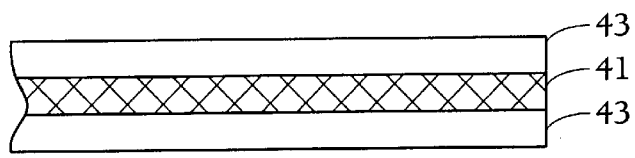
Fig. 10
Fig. 12
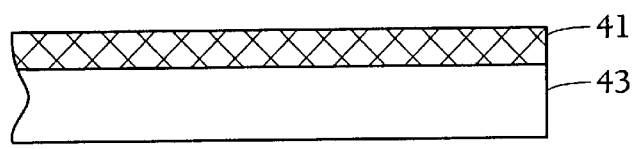
Fig. 11

BREAST IMPLANT WITH POSITION LOCK

BACKGROUND OF THE INVENTION

This invention relates to an improved implantable breast prosthesis and, in particular, to an implantable breast prosthesis that may be anchored in place in a body cavity to reduce postoperative movement of the implant and provide an indication of the orientation of the prosthesis.

Breast prostheses are known which are designed to be implanted behind the breast for reconstruction or augmentation of the mammary gland. These prostheses are made up of an elastomeric envelope or shell delimiting a hermetically closed space which is filled with saline solution, silicone gel or other suitable filling material. Typically, a small periareolar, inframammary, transaxillary, or periumbilical incision is made in the patient and a retroglandular or retropectoral pocket is formed into which the breast prosthesis is inserted. The implant is filled with saline solution or other suitable filling material to a specified volume. The physician verifies the correct orientation of the prosthesis before closing the incision.

A postoperative problem may occur if the implant becomes dislodged from its original placement, creating a noticeable breast deformity. This deformity has been detected in women both within the immediate and long-term postoperative period. Additionally, there is currently no means to diagnose whether the implant has become malpositioned at any time after surgery.

Another difficulty with anatomically shaped breast prostheses is correctly orienting the prosthesis once it has been inserted in the retroglandular or retropectoral pocket. Typically a tab is attached to the posterior surface of the prosthesis in the six o'clock position to provide a way for the physician to correctly position the prosthesis within the pocket. However, when a transaxillary incision is used to insert the prosthesis, the surgeon is not able to reach the tab to verify correct placement of the implant and must rely on visual inspection to ensure the proper orientation of the implant.

SUMMARY OF THE INVENTION

It is therefore the primary object of the present invention to provide an improved breast prosthesis that may be anchored to retroglandular or retromuscular tissue to restrict postoperative movement of the implant.

Another important object of the present invention, as aforesaid, is to provide an improved breast prosthesis with markers to aid the physician in correctly placing the prosthesis during surgery.

Still another important object of the present invention is to provide an improved breast prosthesis with markers to determine postoperative orientation of the prosthesis.

Yet another important object of the present invention is to provide an improved breast prosthesis with radiopaque markers to determine postoperative 3-dimensional orientation of the prosthesis.

These and other objects of the present invention are achieved by providing an improved breast prosthesis having a fastening member secured to the posterior of the flexible shell of the prosthesis which is capable of receiving and holding a suture to secure the prosthesis to the patient's retroglandular or retromuscular tissue. Upper and lower markers on the posterior surface of the flexible shell provide tactile and visual indicators to positively orient the prosthesis during the implantation procedure, as well as reconfirm to the surgeon the implant shape (i.e. round or anatomical). Radiopaque markers provide postoperative location information using standard X-ray equipment to positively determine the 3-dimensional orientation of the implant without use of a surgical procedure.

Other objects and advantages of this invention will become apparent from the following description taken in connection with the accompanying drawings, wherein is set forth by way of illustration and example, an embodiment of this invention.

BRIEF DESCRIPTION OF THE DRAWINGS

FIG. 1 is an elevational posterior illustration of an anatomical breast implant incorporating the improvements of the present invention;

FIG. 2 is a vertical cross-sectional illustration of the anatomical breast implant of FIG. 1;

FIG. 3 is an elevational posterior illustration of a symmetrical breast implant incorporating the improvements of the present invention;

FIG. 4 is a vertical cross-sectional illustration of the symmetrical breast implant of FIG. 3;

FIG. 5 is an elevational posterior illustration of a modified form of the implant of FIG. 1;

FIG. 6 is an elevational posterior illustration of a modified form of the implant of FIG. 3;

FIG. 7 is an elevational view of fastening members combined with a reinforcement ring;

FIG. 8 is an elevational posterior illustration of another modified form of the implant of FIG. 1;

FIG. 9 is an elevational posterior illustration of another modified form of the implant of FIG. 3;

FIGS. 10–12 are enlarged, diagrammatic cross-sectional illustrations of the fastening material;

FIG. 15 is an illustration showing various incision locations;

DESCRIPTION OF THE PREFERRED EMBODIMENT

Figure 13:
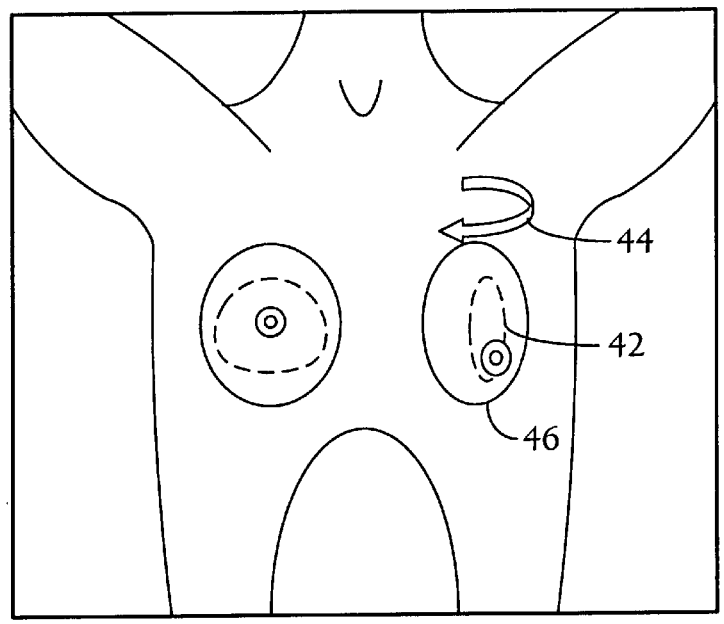
FIG. 13 illustrates a breast deformity caused by a breast implant that has rotated about a vertical axis and out of the original placement.

Turning more particularly to the drawings, an anatomical breast prosthesis of the present invention is generally indicated by reference numeral 20 in FIGS. 1–2, and a symmetrical breast prosthesis is generally indicated by reference numeral 20a in FIGS. 3–4. Prosthesis 20 comprises an outer shell 22, an upper fastening member 24, a lower fastening member 26, an upper marker 28 with two tactile buttons and a lower marker 30 with one tactile button. It should be understood that the difference in the prostheses illustrated in FIGS. 1 and 3 is simply the shape of the outer shell 22 and 22a and the number of upper tactile buttons indicated by 28 and 28a. Corresponding components in the prosthesis of FIGS. 3 and 4 are designated by the same reference numerals with the addition of the "a" notation.

Outer shell 22 is made of a flexible biocompatible material such as room temperature vulcanized silicone, Silastic®, high temperature vulcanized silicone or other material suitable for implanting. Outer shell 22 presents an interior area 32 for containing a suitable filling material such as saline solution, silicone gel, or other material. Outer shell 22 has an anterior area generally indicated by reference numeral 34 and a posterior area generally indicated by reference numeral 36. Outer shell 20a is likewise constructed.

Fastening members 24 and 26 are made of a flexible biocompatible material that is capable of receiving and holding a suture. Fastening members 24 and 26 may be generally rectangularly shaped as illustrated in FIGS. 1, 3, 5 and 6 and in radial alignment in the opposed twelve o'clock and six o'clock positions. The inner end portion of fastening members 24 and 26 are each bonded or otherwise secured to posterior area 36 thereby presenting free ends 25 and 27 illustrated in FIG. 2.

Markers 28 and 30 provide both visual and tactile orientation information to assist the surgeon in correctly orienting the prosthesis 20 when placed in a body cavity. Because anatomical breast prosthesis 20 illustrated in FIG. 1 is asymmetrical, marker 28 is comprised of two semi-spherical buttons that permit the surgeon to determine correct orientation of prosthesis 20. Additionally, a twin-buttoned marker will allow quick confirmation by the surgeon that a deflated implant is indeed an asymmetrical style since both the asymmetrical and symmetrical implants tend to appear similar when deflated. When prosthesis 20 is correctly oriented, the two buttons of marker 28 are in the twelve o'clock position at the top of the breast cavity. Likewise, marker 30 is comprised of a single semi-spherical button that permits the surgeon to correctly orient the prosthesis 20 such that marker 30 is in the six o'clock position at the bottom of the breast cavity. As illustrated in FIG. 3, the orientation of symmetrical breast prosthesis 20a is not important as either marker 28a or 30a may be located in either the twelve o'clock or six o'clock position within the posterior breast cavity with identical results.

A reinforcement ring 38 illustrated in FIGS. 5–6 may be used to provide additional strength to shell 22 where fastening members 24 and 26 are bonded to posterior area 36. Reinforcement ring 38 may be bonded over the interior ends of fastening members 24 and 26 to form a laminate to secure fastening members 24 and 26 to shell 22 or fastening members 24 and 26 may be bonded to the exterior surface of reinforcement ring 38. As illustrated in FIG. 7, the reinforcement ring 38 and fastening members 24 and 26 may be made from the same piece of material and bonded to posterior area 36 of shell 22.

In another embodiment illustrated in FIGS. 8 and 9, fastening member 40 is ring-shaped and bonded to posterior area 36 of shell 22 around the inner portion of the ring under reinforcement ring 38 leaving the outer portion of the fastening ring 40 free. It should be understood that fastening ring 40 may be bonded to posterior area 36 without reinforcement ring 38.

Markers 28, 30, 28a and 30a may be made from a biocompatible material such as Silastic® or a harder plastic or from a radiopaque material. The same is true for fastening members 24 and 26. A radiopaque material such as aluminum, barium, stainless steel, or other suitable material may be embedded in markers 28 and 30 to provide a means to determine the 3-dimensional orientation of the prosthesis once it has been implanted using a common X-ray imaging system, an ultrasound system, or a computerized temography for example, or other noninvasive means.

Fastening members 24 and 26 and fastening ring 40 may consist of a single high strength biocompatible material that is capable of receiving and holding a suture or may be constructed of a reinforced material. Additionally, fastening members may be radiopaque to provide 3-dimensional orientation information as described hereinabove. In the preferred embodiment fastening members 24 and 26 and fastening ring 40 are constructed of Dacron® reinforced Silastic®. The Dacron® layer 41 may be embedded in the Silastic® 43 as shown in FIG. 10, along the upper (or lower surface) as shown in FIG. 11, or along both upper and lower surfaces for added strength as shown in FIG. 12. The locations of the Dacron® 41 or other reinforcing material within the host material such as Silastic® as shown in FIGS. 10–12 are exemplary only. Other materials or combination of materials and placements may be used to achieve the same or similar results.

Figure 14:
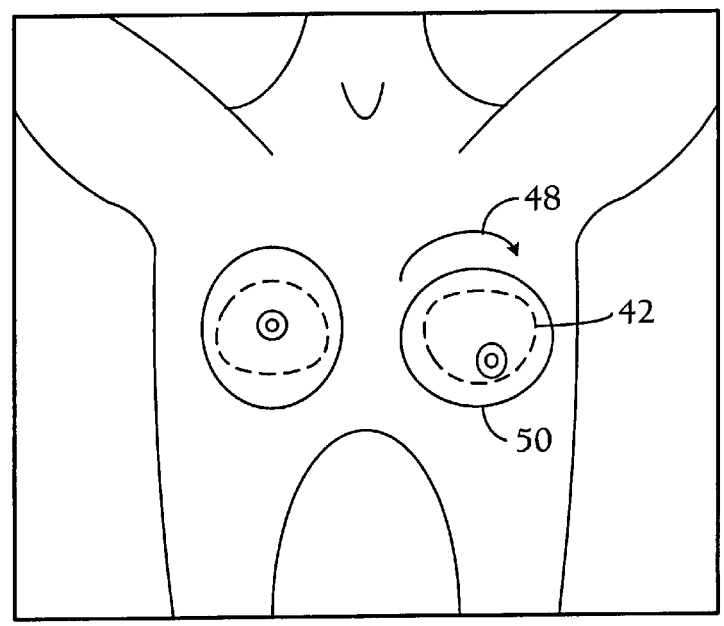
FIG. 14 illustrates a breast deformity caused by a breast implant that has rotated about a horizontal axis and out of the original position.
Figure 16:
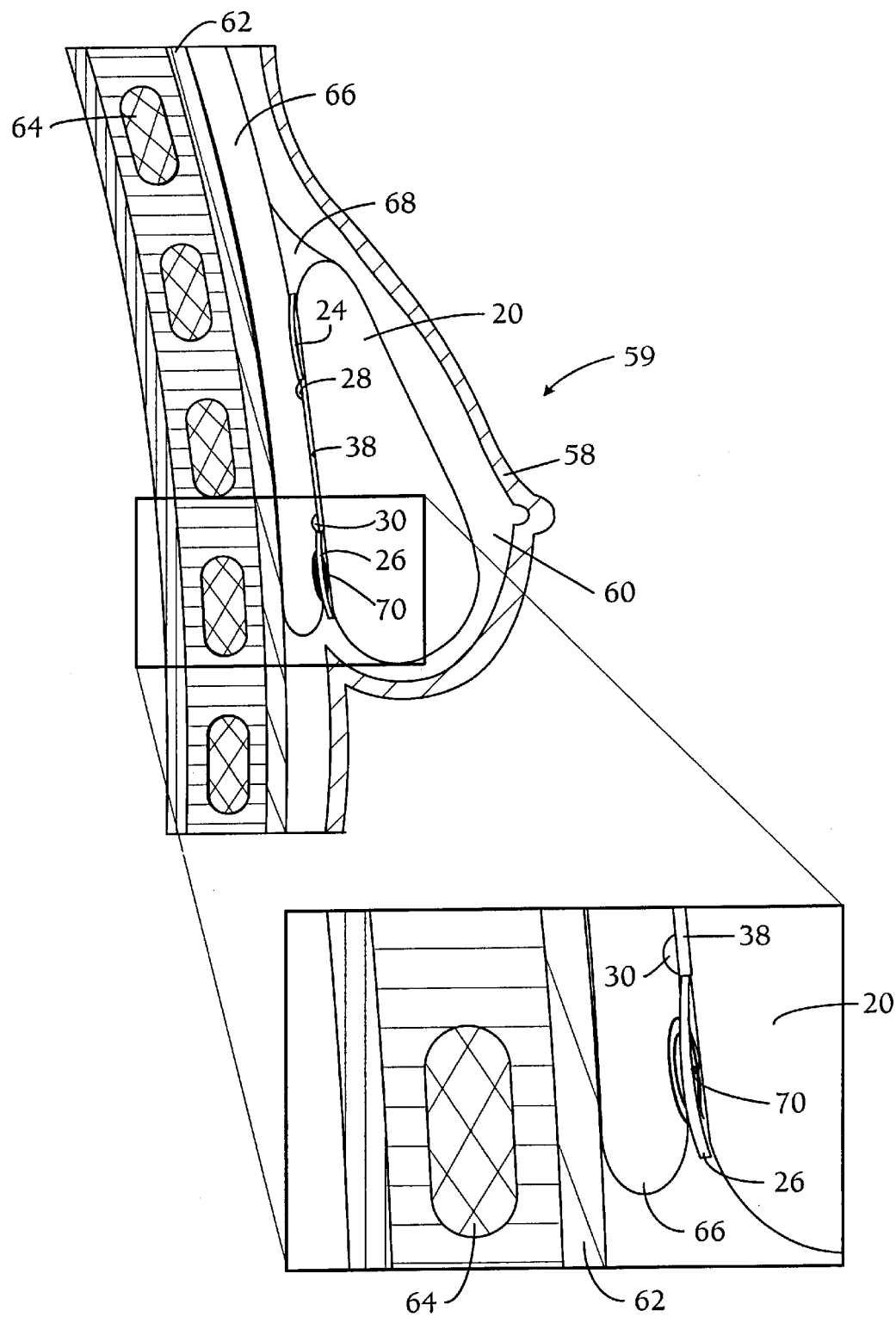
FIG. 16 is a cross-sectional illustration showing an anatomical breast implant anchored to the pectoral muscle fascia by a suture through the lower fastening member.
Figure 17:
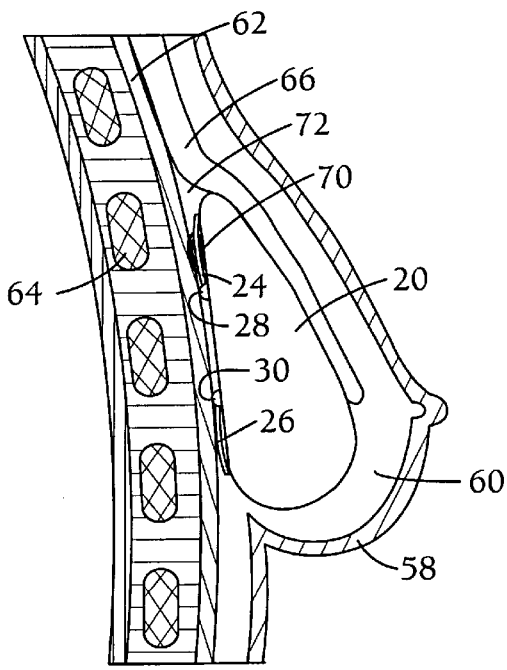
FIGS. 17–20 illustrate upper and lower sutures for retroglandular and retropectoral placements of a breast implant.

FIGS. 13 and 14 illustrate problems that have occurred in prior art breast implants. As illustrated in FIG. 13, an anatomical breast implant 42 may turn or rotate about its vertical axis indicated by direction arrow 44 resulting in a noticeable breast deformity 46. The same problem may occur with a prior art symmetrical breast prosthesis.

As illustrated in FIG. 14, an anatomical breast implant 42 is shown rotated about its horizontal axis indicated by direction arrow 48 resulting in a noticeable breast deformity 50. It should be understood that breast implant 42 may rotate about any axis and is not limited to the two examples shown in FIGS. 13 and 14.

Referring to FIGS. 15–20, three common incision regions are shown (FIG. 15) which include transaxillary 52, periareolar 54, inframammary 56 and periumbilical 57 incisions. The skin incision is made through the dermis 58 of a breast generally indicated at 59, using a scalpel (not shown), and electrocautery (not shown) is then used to incise into the breast tissue 60. The dissection through the breast tissue proceeds either straight posteriorly or by beveling forty-five degrees toward the chest wall 62 which overlaps ribs 64. When the fascia of the pectoralis major muscle 66 is reached, the breast tissue 60 is mobilized off of the pectoralis major muscle 66 if development of a retroglandular pocket 68 is sought. Pocket 68 is precisely formed between the pectoralis major muscle 66 and the breast tissue 60.

Breast implant 20 is inspected for defects and the type of breast implant, anatomical 20 or symmetrical 20a is verified by checking the number of buttons 28 and 28a, then inserted through the incision into the pocket 68. If a periareolar 54 or an inframammary 56 incision is used, implant 20 will be oriented such that the surgeon can feel marker 30 in the six o'clock position toward the bottom of breast 59. With breast implant 20 properly positioned, a suture 70 is located through fastening member 26 or 26a into pectoralis major muscle fascia 66 to anchor implant 20 in place. A figure eight suture 70 or other known stitch may be used. If a transaxillary 52 incision is used, implant 20 will be oriented such that the surgeon can feel marker 28 in the twelve o'clock position toward the top of breast 59. Thus, because of the tactile difference in markers 28 and 30 for an anatomical implant 20, the surgeon can readily distinguish between the top and the bottom of implant 20 for correct orientation.

When performing a retropectoral augmentation (FIGS. 17 and 19), the pectoralis major muscle 66 is lifted up to provide access to the chest wall 62 and form a pocket 72 therebetween. The breast implant 20 is inserted into pocket 72 through the incision and oriented such that marker 30 is in the six o'clock position for a periareolar 54 or inframammary 56 incision. If a transaxillary 52 incision is used, breast implant 20 is oriented such that marker 28 is in the twelve o'clock position toward the top of breast 59. A single figure eight suture 70 is located through lower fastening member 26 (FIG. 19) or upper fastening member 24 into chest wall 62 to lock implant 20 in place.

Figure 18:
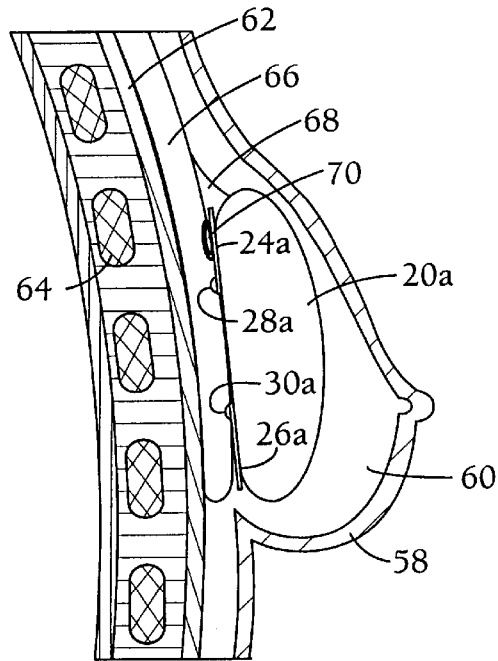
Figure 19:
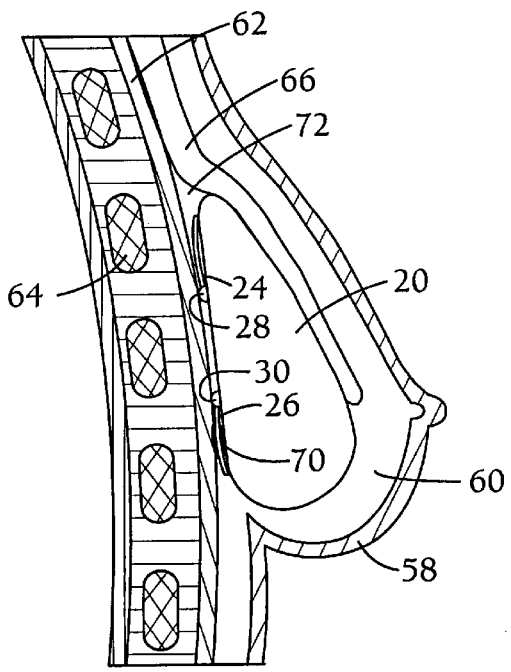
Figure 20:
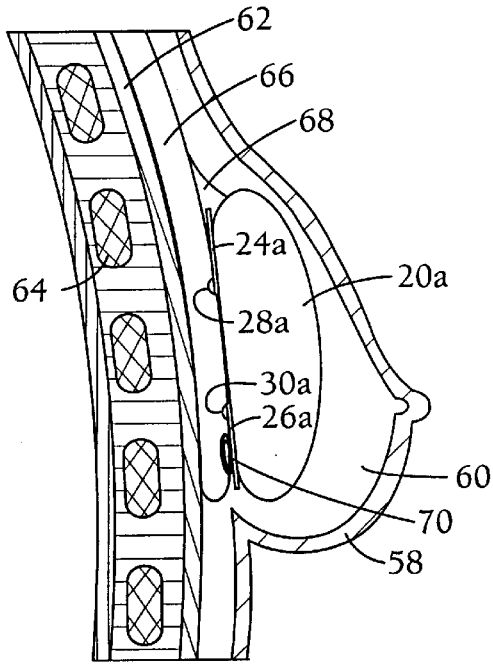

FIGS. 18 and 20 illustrate a retroglandular augmentation mammoplasty utilizing a symmetrical implant 20a. A suture 70 is placed through upper fastening member 24a into pectoralis muscle fascia 66 through a transaxillary incision 52 (FIG. 18). A suture 70 is placed through lower fastening member 28a into pectoralis muscle fascia 66 through a periareolar 54 or an inframammary 56 incision (FIG. 20) to secure breast implant 20a in place. For a symmetrical breast implant, there is no difference in orientation about the horizontal axis, thus markers 28a and 30a are identical.

For larger implants, it may be desirable to anchor implant 20 to pectoralis muscle fascia tissue 66 or chest wall tissue 62 in more than one location such as the ten o'clock and four o'clock positions for added stability and security. Fastening member 40 (FIGS. 8 and 9) may be utilized to provide alternative anchor points for one or more sutures and to provide the surgeon with alternative more convenient or physiologically stable anchor points.

Postoperatively, radiopaque markers 28 and 30, or radiopaque fastening members 24 and 26, provide orientation information on an X-ray image or other non-invasive imaging system to determine if breast implant 20 has shifted or moved from its original implanted position due to trauma to the chest area, for example trauma sustained in an automobile accident, or a routine mammography. The physician may readily determine if a breast deformity is caused by a displaced implant 20 or for some other reason.

It is to be understood that while certain forms of this invention have been illustrated and described, it is not limited thereto, except in so far as such limitations are included in the following claims.

Having thus described the invention, what is claimed as new and desired to be secured by Letters Patent is:

1. A breast implant prosthesis comprising:
    a flexible shell of a predetermined shape composed of biocompatible material for containing a filling material and presenting an anterior area for orientation towards an outer skin surface and an opposed posterior area adapted to overlie internal tissue,
    a fastening component secured to said shell for anchoring said prosthesis, and
    said component comprising a material configured to secure and hold a suture therethrough to secure the component to said tissue and thereby anchor the prosthesis.

2. The apparatus as claimed in claim 1 further comprising a second fastening component secured to an upper portion of said flexible shell for anchoring said prosthesis and wherein said first mentioned fastening component is secured to a lower portion of said flexible shell.

3. The apparatus as claimed in claim 2 wherein said fastening components include radiopaque indicators.

4. The apparatus as claimed in claim 2 wherein said fastening components include tactile indicators.

5. The apparatus as claimed in claim 2 wherein said fastening components provide visual identification of the shape of said shell.

6. The apparatus as claimed in claim 2 wherein said fastening components include Dacron reinforcement.

7. The apparatus as claimed in claim 1 further comprising a marker secured to said flexible shell for identifying an orientation of said prosthesis.

8. The apparatus as claimed in claim 7 further comprising a second marker secured to said flexible shell for identifying said orientation of said prosthesis.

9. The apparatus as claimed in claim 8 wherein said marker provides visual identification of the shape of said shell.

10. The apparatus as claimed in claim 9 wherein said first mentioned marker is secured to an upper portion of said flexible shell in a twelve o'clock position, and said second marker is secured to a lower portion of said flexible shell in a six o'clock position.

11. The apparatus as claimed in claim 9 wherein said first mentioned marker is distinguishable from said second marker.

12. The apparatus as claimed in claim 11 wherein said markers are radiopaque.

13. The apparatus as claimed in claim 11 wherein said markers are tactile.

14. A breast implant prosthesis comprising:
    a flexible shell of a predetermined shape composed of biocompatible material for containing a filling material and presenting an anterior area for orientation towards an outer skin surface and an opposed posterior area adapted to overlie internal tissue,
    a first reinforced fastening component secured to a lower portion of said posterior area for anchoring said prosthesis to said internal tissue,
    a second reinforced fastening component secured to an upper portion of said posterior area for anchoring said prosthesis to said internal tissue,
    said fastening component comprising a material configured to secure and hold a suture therethrough to secure the component to said tissue and thereby anchor the prosthesis,
    a first radiopaque tactile marker on said shell for identifying said first fastening component and visually identifying the shape of said shell, and
    a second radiopaque tactile marker on said shell for identifying said second fastening component.

15. A breast implant prosthesis comprising:
    a flexible shell of biocompatible material for containing a filling material and adapted to contact internal tissue,
    a fastening component having an interior area and a periphery, said interior area secured to said shell for anchoring said prosthesis, and
    said component comprising a material configured to secure and hold a suture therethrough to secure the component to said tissue and thereby anchor the prosthesis.

16. The apparatus as claimed in claim 15 said periphery of fastening component is free.

17. The apparatus as claimed in claim 15 further comprising a marker secured to said flexible shell for identifying an orientation of said prosthesis.

18. The apparatus as claimed in claim 17 further comprising a second marker secured to said flexible shell for identifying said orientation of said prosthesis.

19. The apparatus as claimed in claim 18 wherein said first mentioned marker is secured to an upper portion of said flexible shell in a twelve o'clock position, and said second marker is secured to a lower portion of said flexible shell in a six o'clock position.

20. The apparatus as claimed in claim 19 wherein said first mentioned marker is distinguishable from said second marker.

21. The apparatus as claimed in claim 20 wherein said markers are radiopaque.

22. The apparatus as claimed in claim 20 wherein said markers are tactile.

23. A breast implant prosthesis comprising:
- a flexible shell of predetermined shape composed of biocompatible material for containing a filling material and presenting an anterior area for orientation towards an outer skin surface and an opposed posterior area adapted to overlie internal tissue, and
- a marker secured to said shell configured to visually identify the shape of said shell and identify an orientation of said prosthesis.

24. The apparatus as claimed in claim 23 further comprising a second marker secured to said flexible shell for identifying said orientation of said prosthesis.

25. The apparatus as claimed in claim 24 wherein said first mentioned marker is secured to an upper portion of said flexible shell in a twelve o'clock position, and said second marker is secured to a lower portion of said flexible shell in a six o'clock position.

26. The apparatus as claimed in claim 25 wherein said first mentioned marker is distinguishable from said second marker.

27. The apparatus as claimed in claim 26 wherein said markers include radiopaque identifiers.

28. The apparatus as claimed in claim 23 wherein said marker includes a radiopaque identifier.

29. The apparatus as claimed in claim 23 wherein said marker includes a tactile identifier.

30. The apparatus as claimed in claim 23 further comprising a fastening component secured to said shell for anchoring said prosthesis, and said component comprising a material capable of securing and holding a suture therethrough to secure the component to said tissue and thereby anchor the prosthesis.

31. The apparatus as claimed in claim 30 wherein said fastening component includes a radiopaque identifier.

32. The apparatus as claimed in claim 30 further comprising a second fastening component secured to an upper portion of said flexible shell for anchoring said prosthesis and wherein said first mentioned fastening component is secured to a lower portion of said flexible shell.

33. The apparatus as claimed in claim 32 wherein said fastening components include radiopaque identifiers.

34. The apparatus as claimed in claim 23 further comprising a fastening component having an interior area and a periphery, said interior area secured to said shell for anchoring said prosthesis, and said component comprising a material capable of securing and holding a suture therethrough to secure the component to said tissue and thereby anchor the prosthesis.

35. The apparatus as claimed in claim 34 wherein said fastening component includes at least one radiopaque identifier.

* * * * *